US009407110B2

(12) United States Patent
Lui et al.

(10) Patent No.: US 9,407,110 B2
(45) Date of Patent: *Aug. 2, 2016

(54) SELF-AFFIXING EXTERNAL CHARGING SYSTEM FOR AN IMPLANTABLE MEDICAL DEVICE

(71) Applicant: Boston Scientific Neuromodulation Corporation, Valencia, CA (US)

(72) Inventors: Mun Pook Lui, Northridge, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/530,079

(22) Filed: Oct. 31, 2014

(65) Prior Publication Data

US 2015/0054459 A1 Feb. 26, 2015

Related U.S. Application Data

(63) Continuation of application No. 13/900,844, filed on May 23, 2013, now Pat. No. 8,886,333.

(60) Provisional application No. 61/673,605, filed on Jul. 19, 2012.

(51) Int. Cl.
*A61N 1/00* (2006.01)
*H02J 7/02* (2016.01)
(Continued)

(52) U.S. Cl.
CPC .............. *H02J 7/025* (2013.01); *A61N 1/3787* (2013.01); *H02J 7/0042* (2013.01); *H02J 5/005* (2013.01); *H02J 7/0052* (2013.01)

(58) Field of Classification Search
CPC ...... A61N 1/3787; H02J 5/005; H02J 7/0042; H02J 7/0052; H02J 7/025
See application file for complete search history.

(56) References Cited

U.S. PATENT DOCUMENTS

| 5,314,457 A | 5/1994 | Jeutter et al. |
| 6,505,077 B1 | 1/2003 | Kast et al. |

(Continued)

FOREIGN PATENT DOCUMENTS

| JP | 2004-073725 | 3/2004 |
| WO | 2005/032658 | 4/2005 |
| WO | 2007/124325 | 11/2007 |

OTHER PUBLICATIONS

Invitation to Pay Additional Fees regarding PCT Application No. PCT/US2013/045114 dated Sep. 19, 2013.

(Continued)

*Primary Examiner* — George Manuel
(74) *Attorney, Agent, or Firm* — Lewis, Reese & Nesmith, PLLC

(57) ABSTRACT

An external charging system for charging or powering an implantable medical device is disclosed which is self-affixing to the patient without the need for a holding device. The charging system can comprise a charging coil attached to a flexible member. The flexible member is bendable, and when bent will firmly hold its position on the patient. The system can include an electronics module including a user interface and the necessary electronics for activating the charging coil to produce a magnetic charging field. Wires can couple the charging coil in the coil module to the electronics in the electronics modules. The entire assembly can be encased in a water proof sleeve having a high-friction surface, which protects the charging system and helps the charging system to adhere to the patient.

20 Claims, 12 Drawing Sheets

(51) Int. Cl.
*A61N 1/378* (2006.01)
*H02J 7/00* (2006.01)
*H02J 5/00* (2016.01)

(56) References Cited

U.S. PATENT DOCUMENTS

| | | | |
|---|---|---|---|
| 6,516,227 B1 | 2/2003 | Meadows et al. |
| 6,553,263 B1 | 4/2003 | Meadows et al. |
| 6,658,300 B2 | 12/2003 | Govari et al. |
| 7,078,630 B2 | 7/2006 | Martin-Woodin et al. |
| 7,123,206 B2 | 10/2006 | Hess et al. |
| 7,182,728 B2 * | 2/2007 | Cubb et al. | 600/194 |
| 7,200,504 B1 | 4/2007 | Fister |
| 7,286,880 B2 | 10/2007 | Olson et al. |
| 7,389,138 B2 | 6/2008 | Wagner et al. |
| 7,462,175 B2 | 12/2008 | Chang et al. |
| 8,280,499 B2 | 10/2012 | Brockway et al. |
| 8,321,029 B2 | 11/2012 | Aghassian |
| 8,346,361 B2 | 1/2013 | Bauhahn et al. |
| 8,401,663 B2 | 3/2013 | Aghassian |
| 8,463,392 B2 | 6/2013 | Aghassian |
| 8,498,716 B2 | 7/2013 | Chen et al. |
| 8,626,297 B2 | 1/2014 | Jaax et al. |
| 8,676,318 B2 | 3/2014 | Carbunaru et al. |
| 8,682,444 B2 | 3/2014 | Aghassian et al. |
| 2004/0098068 A1 | 5/2004 | Carbunaru et al. |
| 2005/0143781 A1 | 6/2005 | Carbunaru et al. |
| 2007/0060967 A1 | 3/2007 | Strother et al. |
| 2007/0060980 A1 | 3/2007 | Strother et al. |
| 2007/0124325 A1 | 5/2007 | Moore et al. |
| 2007/0270921 A1 | 11/2007 | Strother et al. |
| 2008/0027500 A1 | 1/2008 | Chen |
| 2009/0024179 A1 | 1/2009 | Dronov |
| 2009/0069869 A1 | 3/2009 | Stouffer et al. |
| 2009/0270951 A1 * | 10/2009 | Kallmyer | A61N 1/3787 607/61 |
| 2010/0305663 A1 | 12/2010 | Aghassian |
| 2010/0331919 A1 | 12/2010 | DiGiore et al. |
| 2011/0234155 A1 | 9/2011 | Chen et al. |
| 2012/0004709 A1 | 1/2012 | Chen et al. |
| 2012/0012630 A1 | 1/2012 | Lui et al. |
| 2012/0053657 A1 | 3/2012 | Parker et al. |
| 2013/0165993 A1 * | 6/2013 | Aghassian et al. | 607/59 |
| 2013/0260677 A1 * | 10/2013 | Partovi | H01F 5/003 455/41.1 |

OTHER PUBLICATIONS

International Search Report and Written Opinion regarding PCT Application No. PCT/US2013/045114 dated Jan. 31, 2014.

* cited by examiner

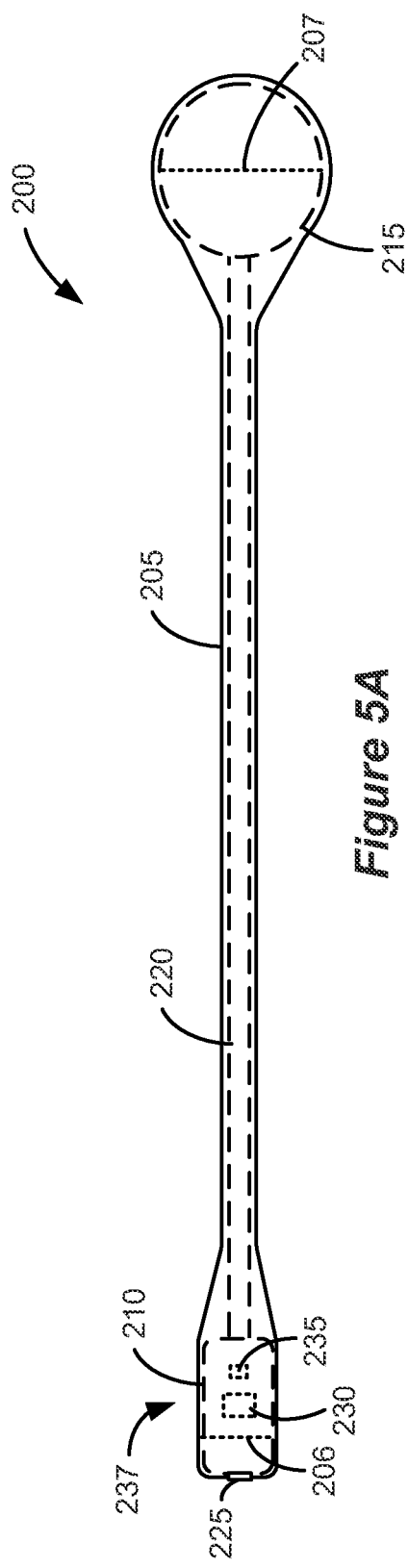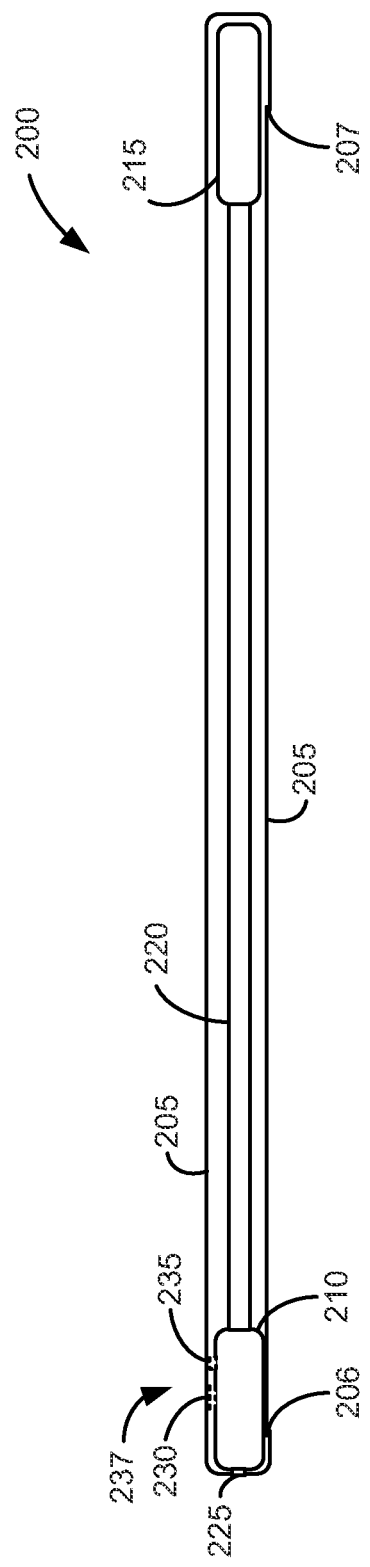

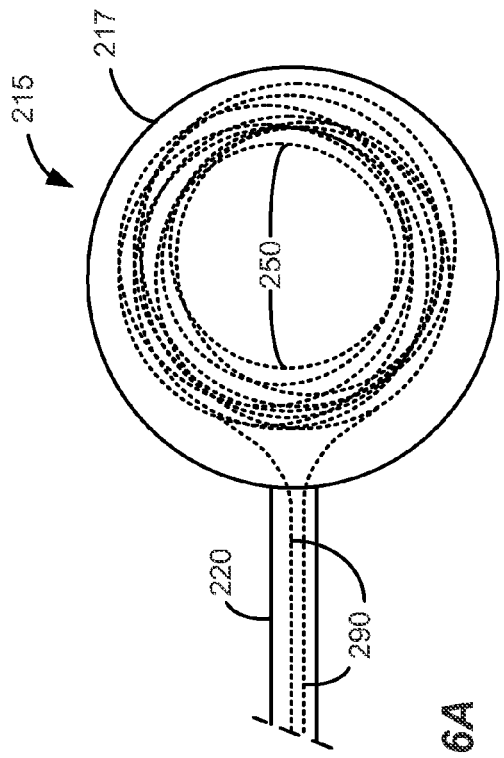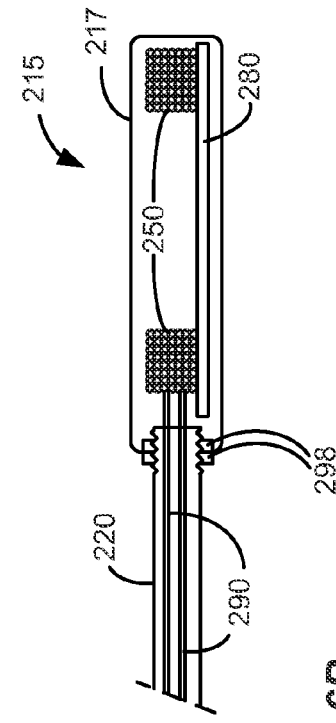
*Figure 6A*
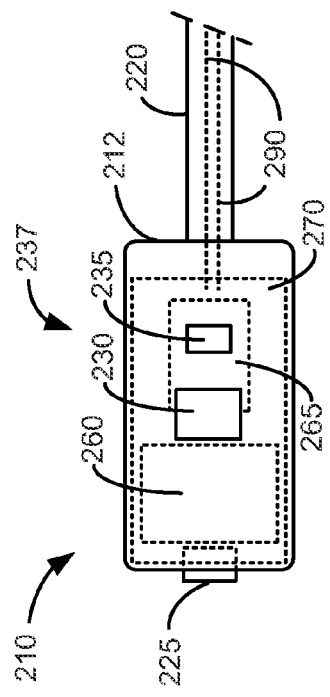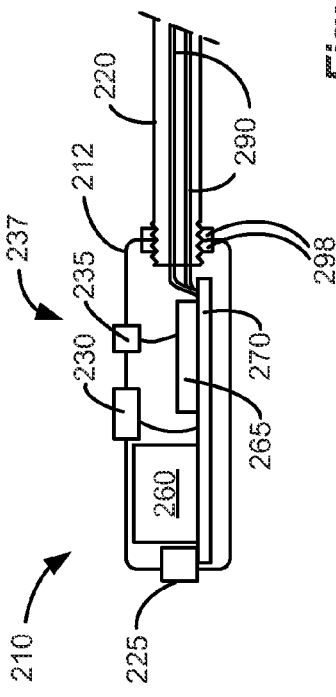
*Figure 6B*

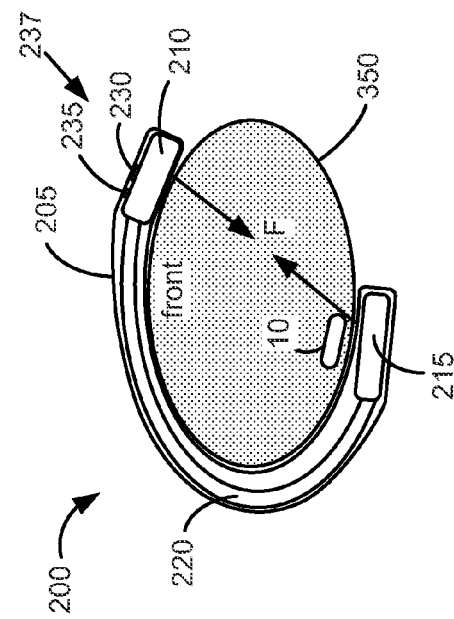
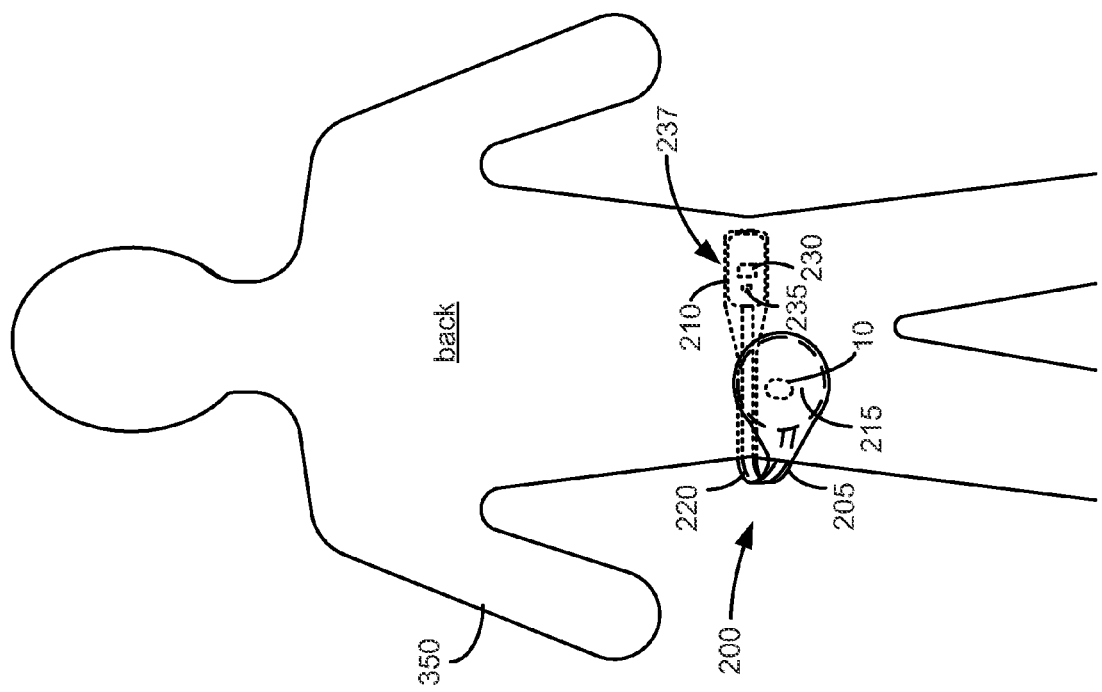
Figure 8

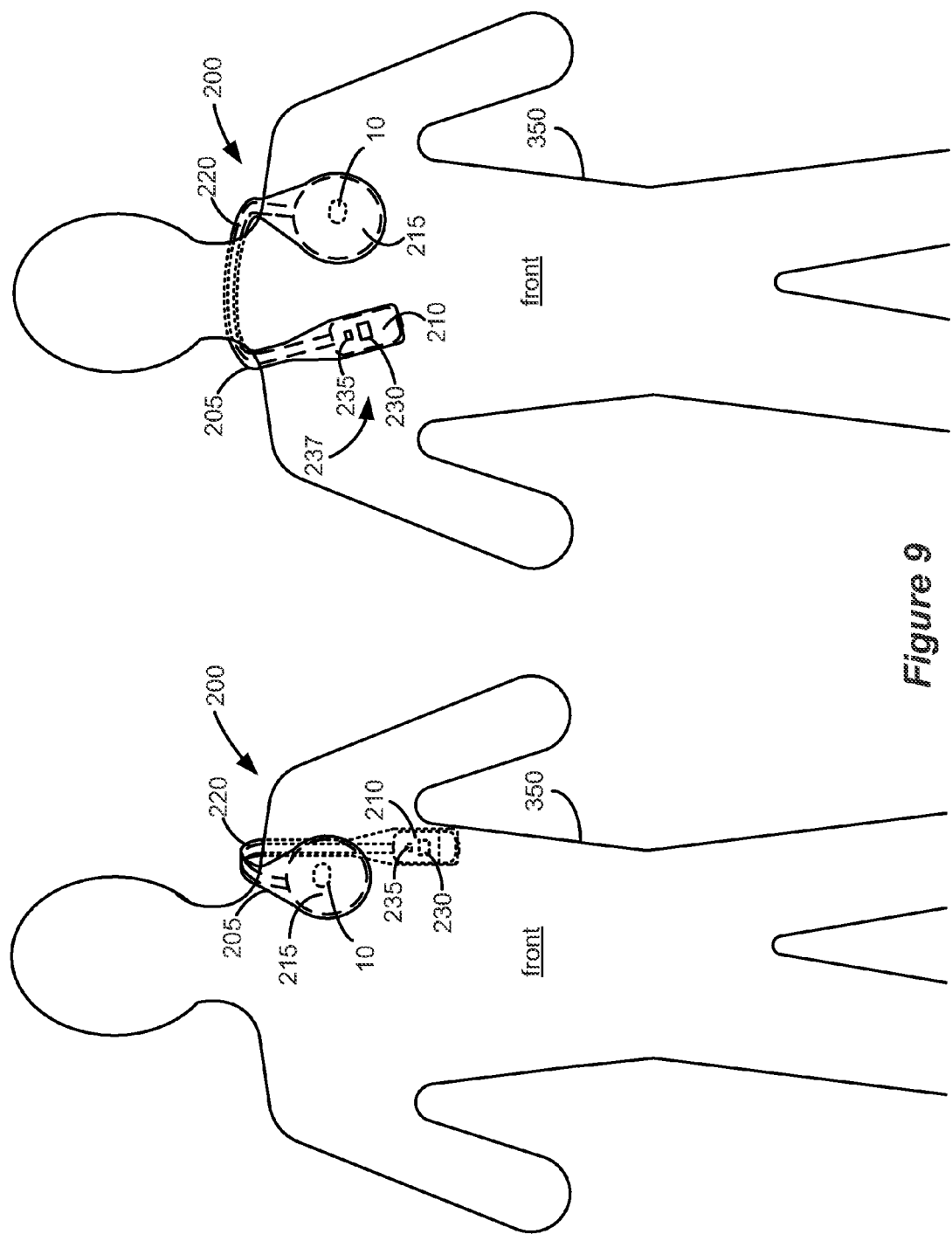

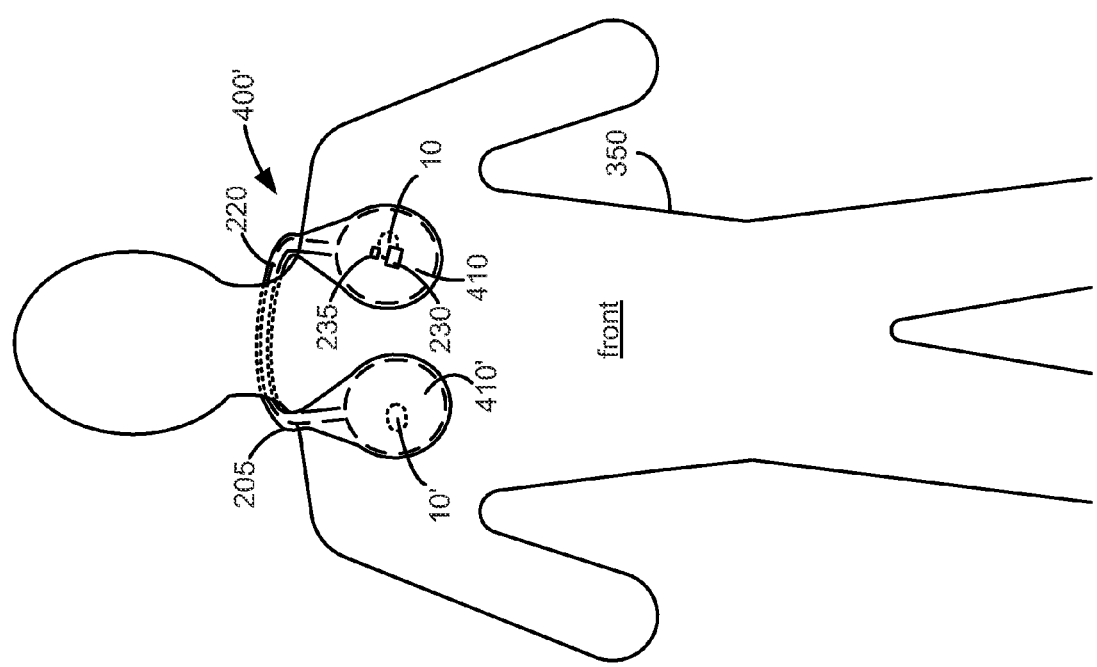

SELF-AFFIXING EXTERNAL CHARGING SYSTEM FOR AN IMPLANTABLE MEDICAL DEVICE

CROSS REFERENCE TO RELATED APPLICATIONS

This is a continuation of U.S. patent application Ser. No. 13/900,844, filed May 23, 2013, now U.S. Pat. No. 8,886,333, which is a non-provisional based on U.S. Provisional Patent Application Ser. No. 61/673,605, filed Jul. 19, 2012, to which priority is claimed, and which is incorporated herein by reference.

FIELD OF THE INVENTION

The present invention relates generally to implantable medical device systems, and more particularly to the design of an external charger for an implantable medical device.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system. However, the present invention is applicable to other implantable medical device system, as will be discussed subsequently.

Spinal cord stimulation is a well-accepted clinical method for reducing pain in certain populations of patients. As shown in FIGS. 1A and 1B, a SCS system typically includes an Implantable Pulse Generator (IPG) 10, which includes a biocompatible case 12 formed of a conductive material such as titanium for example. The case 12 usually holds the circuitry and power source or battery 25 necessary for the IPG to function, although IPGs can also be powered via external RF power and without a battery. The IPG 10 is coupled to electrodes 20 via one or more electrode leads (two such leads 16 and 18 are shown), such that the electrodes 20 form an electrode array 14. The electrodes 20 are carried on a flexible body 22, which also houses the individual signal wires 26 and 28 coupled to each electrode. The signal wires 26 and 28 are connected to the IPG 10 by way of an interface 35, which allows the leads 16 and 18 (or a lead extension, not shown) to be electro-mechanically or remotely (e.g. wirelessly) connected to the IPG 10. Interface 35 may comprise lead connectors 36 and 38 embedded in a non-conductive header 40, which can comprise an epoxy for example. The header 40 can further include a telemetry antenna or coil 42 for receipt and transmission of data to an external device such as a portable or hand-held external controller (not shown).

As illustrated, there are eight electrodes on lead 16, labeled $E_1$-$E_8$, and eight electrodes on lead 18, labeled $E_9$-$E_{16}$, although the number of leads and electrodes is application specific and therefore can vary. The electrode array 14 is typically implanted along the dura of the spinal cord, and the IPG 10 generates electrical pulses that are delivered through the electrodes 20 to the nerve fibers within the spinal column. The IPG 10 is typically implanted somewhat distant from the leads 16 and 18, such as in the upper portion of the patient's buttocks (see FIG. 3).

As shown in cross-section in FIG. 2, an IPG 10 typically includes a printed circuit board (PCB) 44 containing various electronic components 46, such as microprocessors, integrated circuits, and capacitors. Ultimately, the electronic circuitry performs a therapeutic function, such as neurostimulation. A feedthrough 49 routes the various electrode signals from the electronic circuitry to the lead connectors 36 and 38, which are in turn coupled to the leads 16 and 18 as mentioned previously.

Also shown in FIG. 2 is an external charger 50 that is used to power the IPG 10, commonly by recharging the battery 25 in the IPG 10. The external charger 50 itself needs power to operate, and therefore may include its own battery 52, which may also be rechargeable using a plug-in-the-wall holster ("cradle") or power cord connection. Alternatively, the external charger 50 may lack a battery 52 and instead draw its power directly from being plugged into a wall outlet (not shown).

The external charger 50 can contain one or more PCBs 54, which contain the circuitry 56 needed to implement its functionality. The external charger 50 comprises a case or housing 58, typically formed of a hard plastic, which may be divided into top and bottom portions 58a and 58b. The case 58 can be hand-held, body-worn, and/or portable. Junction 59 illustrates the location where the top and bottom case portions 58a and 58b may be snapped together or connected by other means. Clamps 60 may be utilized to hold the PCB 54 and other internal structures in place.

The charger 50 typically includes an alternating current (AC) coil 62, which generates an AC magnetic field to supply power 64 to the IPG 10. The magnetic field induces an AC current in a charging coil 48 located in or on the IPG 10 via inductive coupling. This means of inductive power transfer can occur transcutaneously, i.e., through the patient's tissue 80. The power 64 received by the IPG's coil 48 can be rectified and used to recharge battery 25 in the IPG 10, which in turn powers the IPG 10. Alternatively, power 64 can directly power the IPG if it lacks a battery.

External charger 50 typically employs a relatively simple user interface 70, which simplicity is warranted because of the relative simplicity of the charging function, and because the external charger 50 may not be visible to the patient while in use, thus limiting the utility of more complex visual user interfaces. The user interface 70 of the external charger 50 typically comprises an on/off switch 72 that activates the charger to produce power 64, an LED 74 to indicate the status of the on/off switch, and a speaker 76 for emitting a "beep" at various times, such as when the external charger 50 is not properly aligned with the IPG 10 or when charging has completed.

To provide efficient power transfer, i.e., good coupling, from coil 62 to coil 48, the coils 62 and 48 are preferably wrapped in planes that are substantially parallel during a changing session. Good coupling is also promoted when the coils 62 and 48 are as close as possible, and when the axes around which they are wound are aligned, i.e., when the coils 62 and 48 and centered. Good coupling increases the power 64 transferred from the external charger 50 to the IPG 10, which as well as being efficient, minimizes heating in the IPG 10 and the external charger 12. Proper coupling may also be required for data transfer between the IPG 10 and the external charger 12.

Because charging the battery 25 in the IPG 10 may some time, it is desired to hold the external charger 12 in close proximity to and in alignment with the IPG 10 during a charging session. Typically, this occurs using an external charger holding device 100, such as a belt 102, as shown in FIG. 3. The belt 102 fastens around the patient's waist, and can be secured by a fastening device 108, such as a buckle, clasp, snaps, Velcro, etc. The belt 102 can be adjustable to fit patients with different waist sizes. The belt 102 includes a pouch 104, which generally hangs from the belt 102 in a position where the IPG 10 is implanted in the patient's buttocks. A slot 106 or other opening in the belt 102 allows the external charger 50 to be inserted into the pouch 104, such that the external changer 50 is, like the pouch 104, generally aligned with the IPG 10. Once placed in the pouch 104, the patient can press the on/off switch 72 on the external charger 50 to begin a charging session, or the user can turn the charger on before inserting it in the pouch 104. Affixing the external charger 50 to the patient using belt 102 allows the patient to move or walk while using the external charger 50, and thus can charge his implant "on the go." See also U.S. Patent Application Publication 2012/0012630, describing another belt for an external charger.

While an external charger holding device 100 such as a belt 102 performs suitably to generally hold the external charger 50 in alignment with the IPG 10 in an SCS application, the inventors have noticed certain shortcomings with this approach. First, belt-style holding devices may work well for implantable medical device implanted around the waist region, but are not generally suited for holding and positioning the external charger 50 at other locations in the body where devices can be implanted. The fastening means 108 can break or wear out. Belt-style holding devices also require two pieces—the external charger 50 and the belt 102—which the patient must keep track of. Additionally, belt-type holding devices may shift as the patient moves, which can require the patient to keep adjusting the position of the belt to achieve good alignment with the IPG 10.

Additionally, belt-style holding devices do nothing to address heating in the external charger 50. As discussed elsewhere, see, e.g., U.S. Patent Application Publications 2008/0027500; 2011/0234155; 2011/0178576; and 2011/0071597, the magnetic charging field generated by coil 62 tends to generate heat in the external charger 50. Such heating can occur when the magnetic field interacts with other conductive structures in the external charger 50, such as the PCB 54, the battery 52, and other electronic components 56. The magnetic field induces Eddy currents in such conductive structures, which will heat because of their resistance. Heating is an important consideration in an external charger 50, because it runs the risk of irritating or hurting the patient, particularly given that the external charger 50 is typically in contact with the patient. Unwanted coupling of power to conductive components in the external charger 50 further reduces the power 64 available for charging the IPG 10. While the above-cited publications discuss ways to address such concerns, belt-style holding devices by themselves do nothing to address such concerns, as they do involve any redesign of the external chargers themselves. In fact, the present inventors realize that by encompassing the external charger 50 in a pouch 104, such holding devices tend to exacerbate heating concerns, because the pouch 104 insulates the external charger 50 to some degree and thus doesn't permit heat to radiate away from the external charger.

Another prior art system 150 is shown in FIG. 4, and is disclosed in U.S. Patent Application Publication 2009/0118796, which is incorporated herein by reference, and with which the reader is assumed familiar. System 150 comprises an external controller 152 able to bi-directionally wirelessly communicate with the telemetry coil 42 (FIG. 1A) in the IPG 10. This is useful for example to allow a patient to change the therapeutic setting of his IPG 10 using a graphical user interface comprising a screen 154 and various buttons 156, or to monitor various data of interest from the IPG 10. In addition to this communicative function, the external controller 152 is also coupleable to an external charging coil assembly 160 containing a charging coil 162. The external controller 152 contains electronics and programming for energizing the charging coil 162 with an AC current, thus producing a magnetic charging field for charging the IPG 10. That is, by attaching the external charging coil assembly 160 to the external controller 152, the system 150 becomes in effect an external charger, controlled using the external controller 152's user interface and circuitry. When charging of the IPG 10 is unnecessary, the external charging coil assembly 160 can be detached from the port 164 on the external controller 152, which can now resume its normal function of communicating data with the IPG 10.

The combined external controller 152 and external charging coil assembly 160 is beneficial for the reasons stated in the '796 Publication. Furthermore, and although not discussed in the '796 Publication, the present inventors recognize this prior art system is beneficial from a heating perspective. Because the conductive structures in the external controller 152 (a PCB, a battery, etc.) are distant from the charging coil 162, the magnetic field produced by the charging coil 162 will not significantly induce Eddy currents in such structures. The present inventors realize that this reduces heating in the system 150, and reduces power loss to such components.

Still, the system 150 still has to be affixed to the patient during a charging session. The external charging coil assembly 160 is attached to the external controller 152 by a cable 166 comprising wires. Thus, even if the patient is holding the external controller 152 portion of the system in his hand, or has put the external controller 152 is his pants pocket for example, the external charging coil 162 would still have to be affixed to the patient to hold it into alignment with the IPG 10. Thus, and although not discussed in the '796 Publication, at least the external charging coil assembly 162 (and possibly also the external controller 152) would still need to be inserted into a belt type-holding device such as shown in FIG. 3, particularly if the patient wants to move or walk while charging. This is inconvenient for the reasons stated above.

An improved design for an external charger for an implantable medical device, and an improved means for affixing the external charger to a patient during a charging session, is therefore desired. It is further desired that such improved design be able to charge implantable medical devices wherever they are implanted in a patient.

BRIEF DESCRIPTION OF THE DRAWINGS

FIGS. 5A and 5B show a first example of the improved charging system having a flexible member adjoining an electronics module and a coil module.

FIGS. 6A and 6B show internal details of the improved charging system.

FIG. 8 shows how the improved charging system can be self-affixed to a patient having an IPG in a Spinal Cord Stimulator (SCS) application.

FIG. 9 shows how the improved charging system can be self-affixed to a patient having an IPG in a Deep Brain Stimulation (DBS) application.

FIG. 11 shows how the improved charging system of FIGS. 10A-10C can be self-affixed to a patient having two IPGs in a Deep Brain Stimulation (DBS) application.

DETAILED DESCRIPTION

Figure 1:
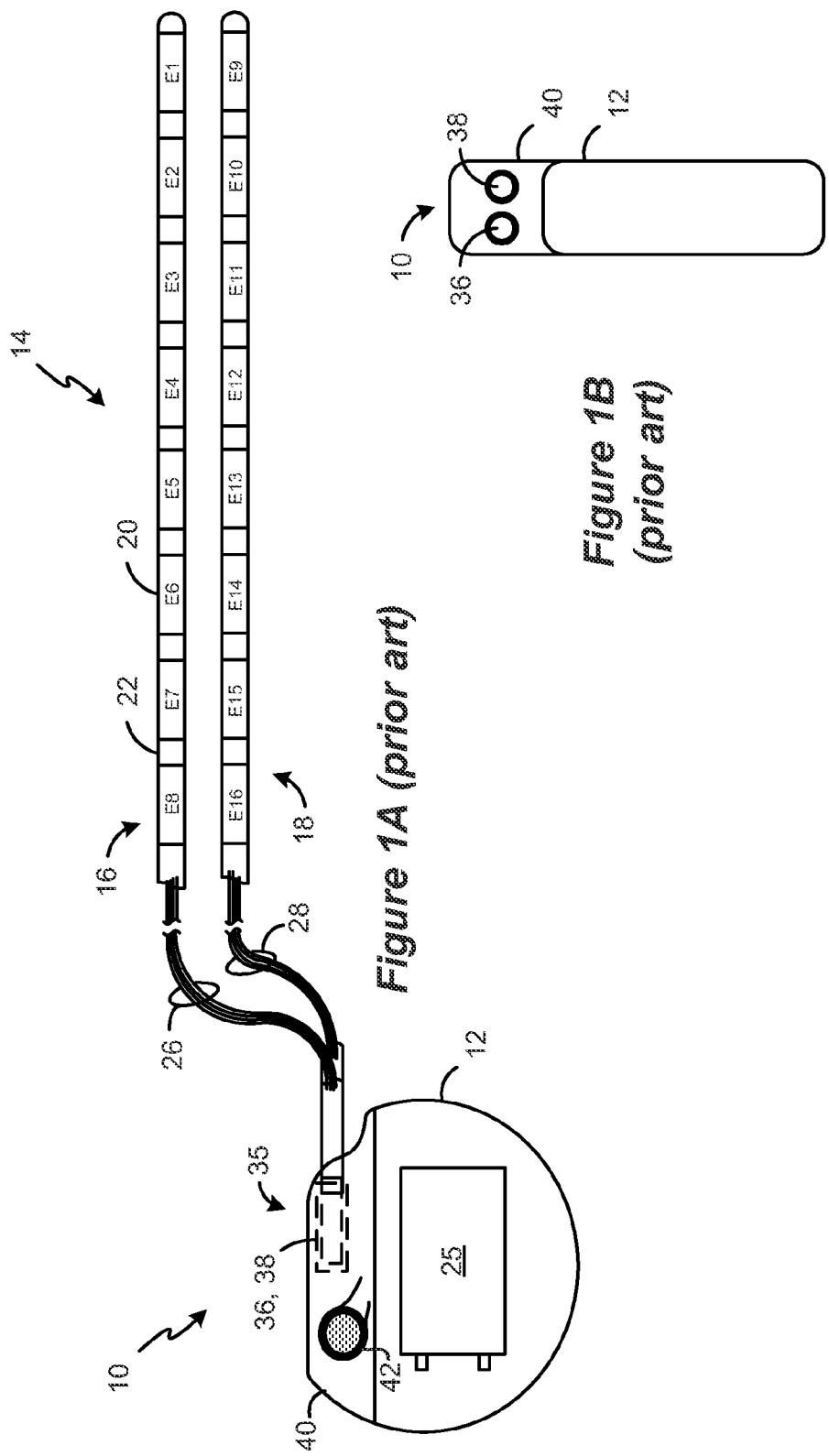
FIGS. 1A and 1B show an implantable pulse generator (IPG) in accordance with the prior art.

An external charging system for charging or powering an implantable medical device is disclosed which is self-affixing to the patient without the need for a holding device. In one example, the charging system comprises two modules attached to opposite ends of a flexible member. The flexible member is bendable around the patient, and when bent will firmly hold its position on the patient. In one example, the two modules can comprise a coil module containing a charging coil, and an electronics module including a user interface and the necessary electronics for activating the charging coil to produce a magnetic charging field, such as a battery, a microcontroller, and charging circuitry. Wires can couple the charging coil in the coil module to the electronics in the electronics modules, which can run through or along side the flexible member. The entire assembly can be encased in a water resistant sleeve having a high-friction surface, which protects the charging system and helps the charging system to adhere to the patient.

In use, the coil module of the charging system is aligned over the patient's implant, and then the flexible member is bent in any convenient fashion around the patient to affix the charging system to the patient. This design allows patients to recharge implantable medical devices wherever they are implanted in a patient. Additionally, when the coil is separated from the electronics, heating is reduced, and the coil can produce larger magnetic fields and can charge an implant more quickly.

FIG. 5A shows a top down view and FIG. 5B shows a side cut-away view of an embodiment of the improved self-affixing charging system 200. The charging system 200 comprises an electronics module 210 and a coil module 215 which are connected by a flexible member 220. These components 210, 215 and 220 are preferably encased in a sleeve 205. The sleeve 250 has openings 206 and 207 to allow components 210, 215, and 220 to be inserted in the sleeve during manufacture. Thereafter, these openings 206 and 207 can be closed using flaps, snaps, or Velcro, or in any other number of ways, or they can be permanently sealed closed by the manufacturer, for example, by heat sealing. In one example, the sleeve 205 can comprise a fabric with a rubbery or high-friction surface that allows the charging system 200 to adhere to the patient or his clothing, as will be discussed further below. In one embodiment, the sleeve 205 can comprise SuperFabric® (a registered trademark of Higher Dimension Materials, Inc.). As well as having some friction, the sleeve 205 is preferably also water resistant to allow it to be easily cleaned by the patient, and to protect the inner electronics from water damage.

Figure 2:
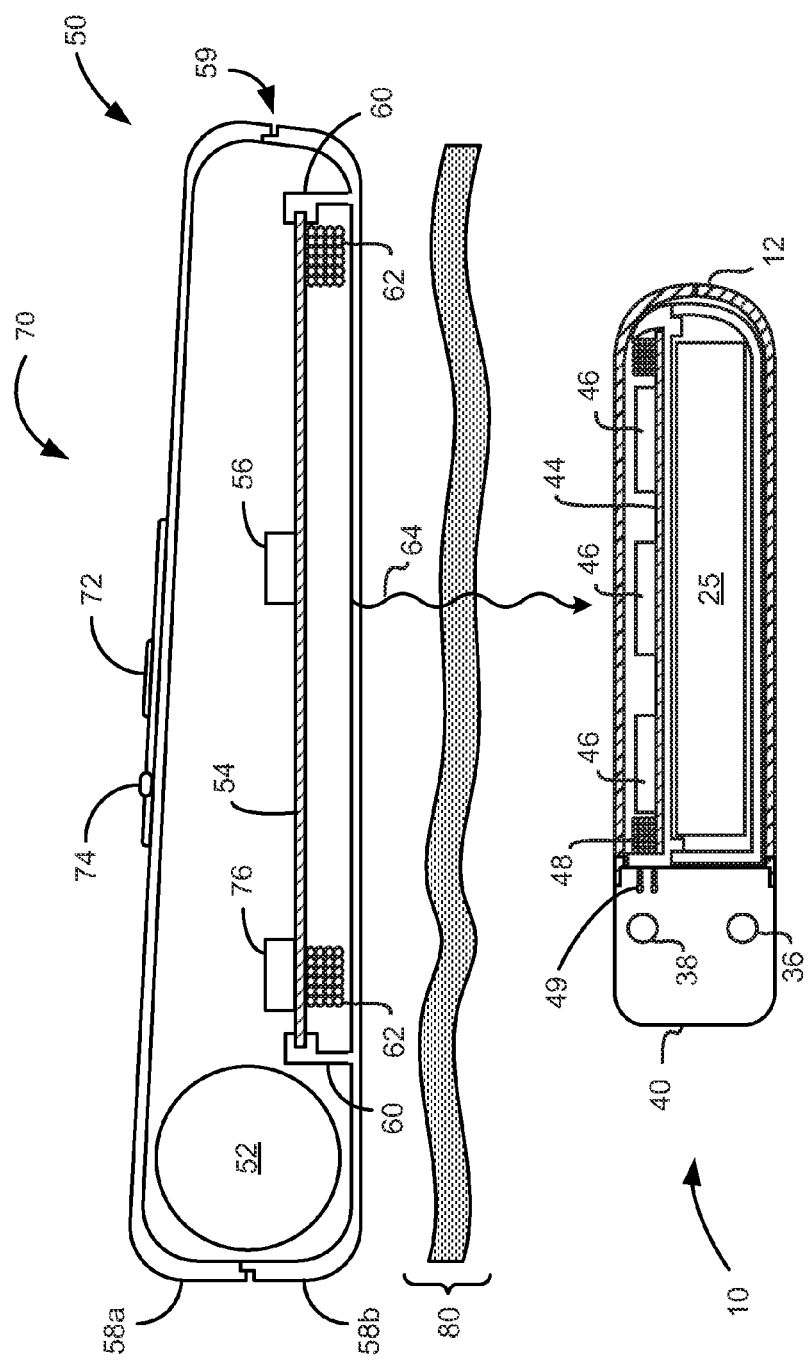
FIG. 2 shows a cross section of the IPG and an external charger used to charge or power the IPG in accordance with the prior art.
Figure 4:
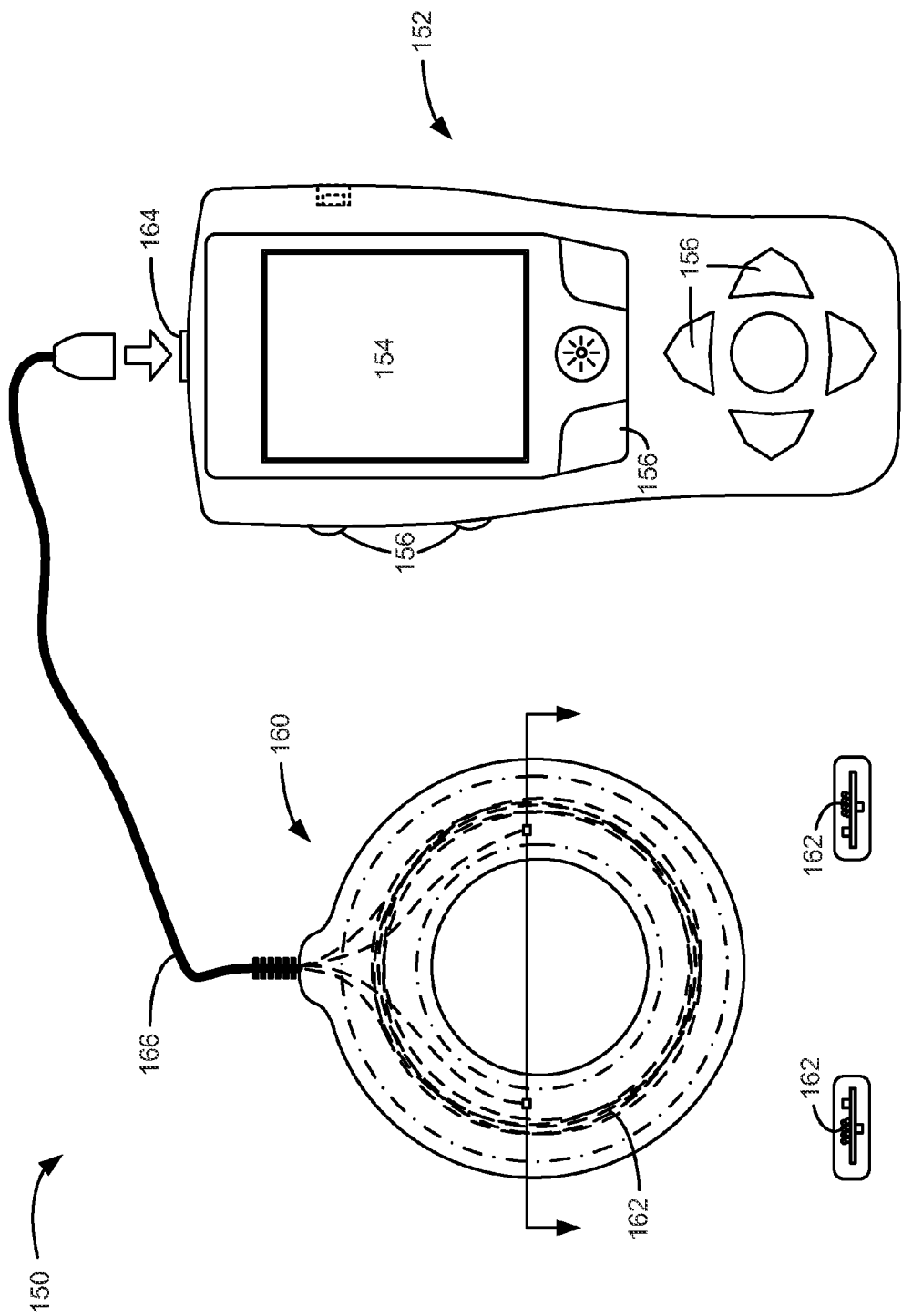
FIG. 4 shows an alternative external charger in accordance with the prior art having a detachable charging coil.

While the components within the charging system 200 are generally covered by the sleeve 205, a port 225 preferably passes through the sleeve 205 to allow the battery 260 in the electronics module 210 to be charged, and/or to allow computer access to the charging circuitry 265 in the electronics module, as discussed below. However, port 225 is not strictly necessary, particular if the charging system 200 is rechargeable by inductive means. Additionally, the electronics module 210 contains a user interface 237, including an on/off switch 230 and an LED 235. (Other aspects of the user interface 237, such as a speaker and optional display 310, are discussed later). The switch 230 and LED 235 may also pass through the sleeve 205, but this is not strictly if the patient can feel and push the switch 230 through the sleeve, and if the LED 235 is bright enough to be seen through the sleeve. The on/off switch 230 and LED 235 serve the same function as switch 72 and LED 74 described earlier (FIG. 2), namely to turn charging on and off, and to indicate the same to the patient. Thus, with the possible exception of the port 225, the charging system 220 can be entirely covered by the sleeve 205, and no wires (compare cable 166; FIG. 4) or connections (compare port 164; FIG. 4) are exposed. This improves system reliability, as wires or connections may be susceptible to damage from liquids, electrical shock, mechanical failure, etc.

FIG. 6A shows a top down view and FIG. 6B shows a side cross sectional view of the charging system 200, with the sleeve 205 removed for easier viewing. The electronics module 210 includes an electronics housing 212 in the example shown, which contains the charging circuitry 265 and a battery 260 coupled to a Printed Circuitry Board (PCB) 270. Battery 260 preferably powers all of the components in the electronics modules 210, and to drive the coil 250 as well. Port 225, switch 230, and LED 235 also couple to the PCB 270. The electronics housing 212 can be hard plastic in one example, similar to the external charger case 58 described earlier and having top and bottom portions that can be snapped or bolted together. While beneficial to protect the components, a housing 212 is not strictly required for the electronics module 210.

The coil module 215 likewise comprises a coil housing 217 in the example shown, which again may be hard plastic, but which may also be soft and flexible to conform to the patient's body. See, e.g., the above-incorporated '796 Publication. The coil housing 217 houses a charging coil 250. Like the charging coils 62 and 162 of the prior art (FIGS. 2 and 4), charging coil 250 will emit a AC magnetic field to power the IPG 10 or otherwise charge its battery 25. As shown, the charging coil 250 is affixed to a PCB 280. However, PCB 280 is not strictly necessary, and the charging coil 250 could also be rigidly affixed inside the coil housing 217, for example, using epoxy. Having a PCB 280 however may make the placement of other electronic devices easier in the coil housing 217, such as thermistors 295 for measuring temperature, which is not shown in FIGS. 6A and 6B, but is later discussed. Epoxy can also be used as the housing 217 for the charging coil 250. Again, a housing 217 is not strictly required for the coil module 215.

The flexible member 220 comprises a structural support that is linear between the modules 210 and 215, and may comprise a flexible metal tube, such as a gooseneck tube. A gooseneck tube comprises a spiral-wound core of steel, and when bent to a desired position will hold that position. (Gooseneck tubes are commonly used in adjustable microphones and table lamps, as one skilled in the art will understand). As will be discussed further below, the flexible member 220 allows the electronics module 210 to be bent with respect to the coil module 215, which therefore allows charging system 200 to be affixed to a patient in a proper position to charge the patient's implantable medical device. Gooseneck tubing can also take the form of flexible jointed metal pipes, and can be made of flexible plastic materials; a non-conductive flexible member 220 may be more desirable because it would not interfere with the magnetic field generated by the charging coil 250. Flexible member 220 need not be circular in cross section; for example, it could also be relatively planar, such as in the form of a flexible sheet or flat band.

If implemented as a flexible tube, the flexible member 220 can contain wires 290 to connect the ends of the charging coil 250 in the coil module 215 to the electronics in the electronics module 210, such that the tube protects the wires 290. However, it is not strictly necessary that flexible member 220 comprise a tube, or be hollow, and instead any wires 290 running between the modules 210 and 215 can also run along side the flexible member 220, in which case they would only be protected by the sleeve 205 (not shown). If non-tubular, the flexible member 220 can comprise a memory metal or any other well-known flexible member capable of holding its bent position.

Flexible member 220 can be affixed to modules 210 and 215 in any number of ways. For example, the flexible member 220 can comprise threaded ends as shown in FIG. 6B, and nuts 298 can be screwed onto the threads on one or both sides of the housings 212 and 217 to hold the flexible member 220 in place relative to the modules 210 and 215. The flexible member 220 can however be mechanically coupled to the modules 210 and 215 in other ways. In another example, top and bottom cases portions of housings 212 and 217 can be affixed together and clamped around the flexible member 220 to hold it in place.

Figure 7:
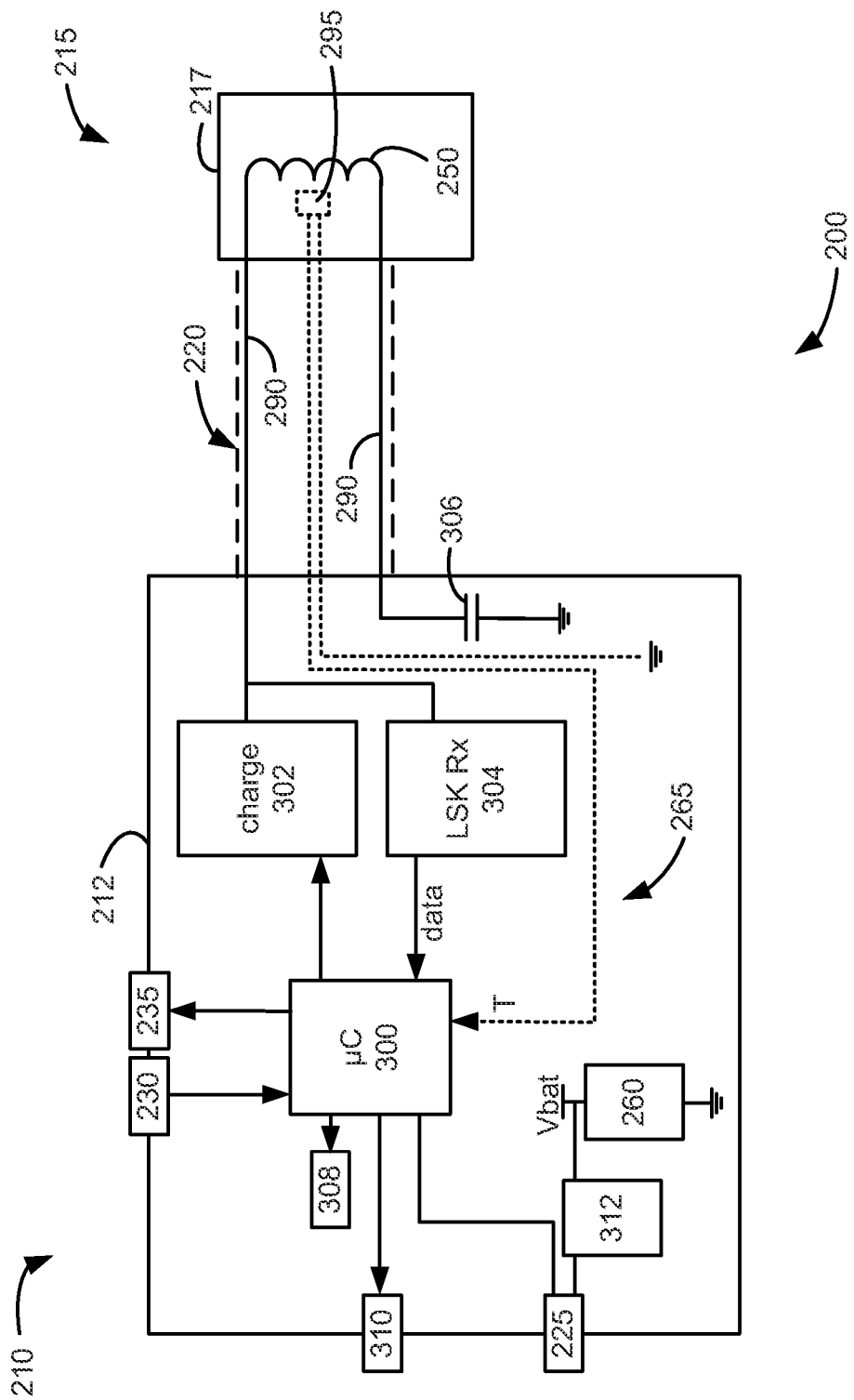
FIG. 7 shows circuitry in the improved charging system.

FIG. 7 shows a circuit diagram of the charging system 200. The electronics module 210 includes a microcontroller 300 for implementing the functionality of the system. Port 225 (e.g., a USB port) can be used to update the software in the microcontroller 300 if necessary, or to read data out of the system. The port 225, as mentioned earlier, can also be coupled to a source of power, such as a wall outlet, to allow the battery 260 to be recharged. Battery charging circuitry 312, which may include rectifier circuitry if AC power is present at the port, can control battery 260 recharging. The battery 260 ultimately powers all components in the charging system 200. Alternatively, the charging system 200 can lack a battery, and can instead by plugged into a wall outlet at port 225.

When the on/off switch 230 is pushed, the microcontroller 300 enables coil driving circuitry 302, which will drive the charging coil 250 with an AC signal of a frequency desired for the magnetic charging field (e.g., approximately 80 kHz). A capacitance of a capacitor 306 and an inductance of the charging coil 205 are chosen such that their serial connection will generally resonate at this frequency. Wires 290 passing through the flexible member 202 connect the coil driving circuitry 302 to one end of the coil 250, and connect the capacitor 306 to the other end of the coil. During provision of the magnetic field, the IPG 100 can communicate back to the charging system using Load Shift Keying (LSK), and an LSK receiver 304 can be used to demodulate the transmitted data. As explained in U.S. Patent Application Publication 2011/0112611, such a means of telemetry is useful to allow the IPG 10 to inform the charging system 200 when the IPG's battery 25 is full, and thus charging can cease. Speaker 308 can inform the patient when this occurs, and can also be used to indicate misalignment between the charging coil 250 and the IPG 10, as discussed previously. A vibratory motor (not shown) could also be used to provide feedback of system operation to the patient. Optional thermistors 295 can also be placed in the coil module 215 to monitor temperature, and if so, additional wires to those thermistors 295 can pass through or along side the flexible member 220.

FIG. 8 shows how the charging system 200 can be affixed to a patient 350 to charge or power an implant in a SCS application in which the IPG 100 is implanted in a patient's upper buttocks. Viewing the patient 350 from the back at the left of FIG. 8, it is seen that the patient has bent the flexible member 220 such that the coil module 215 is aligned with the IPG 10 behind the patient. The electronics module 210 by contrast is bent in front of the patient 350. (If the patient is thin, and although not shown, the flexible member 220 can be bent upwards or downwards to keep the electronics module 210 in front of the patient, or the electronics module 210 can be wound around to the back of the patient). The charging system 200 stays firmly in place to charge the IPG 10. When the flexible member 220 is bent to hold the position shown, it places a force F on the patient 350, as shown in the cross section. Essentially, the charging system 200 can gently pinch the patient 350, thus affixing the system to the patient all by itself. Moreover, self-affixing the charging system 200 in place is assisted by the friction of the sleeve 205, regardless whether the system is in contact with the patient's skin directly, or, as is more common, the patient's clothes (not shown). Such forces allow the patient to charge his IPG 100 even while walking.

Typical patient waist circumferences can range from 25 to 66 inches, and therefore, the length of the flexible member 220 between the two modules 210 and 215 could be at least 70% of these values (i.e., from about 17 inches to about 46 inches) to ensure that the charging system 200 will suitably wrap around a patient's waist. In one example, a manufacturer could produce two charging systems of differing flexible member 220 lengths: one of 46 inches (to accommodate patients with waist sizes between 40 to 66 inches), and one of 29 inches (to accommodate patients with waist sizes between 25 to 42 inches).

Figure 3:
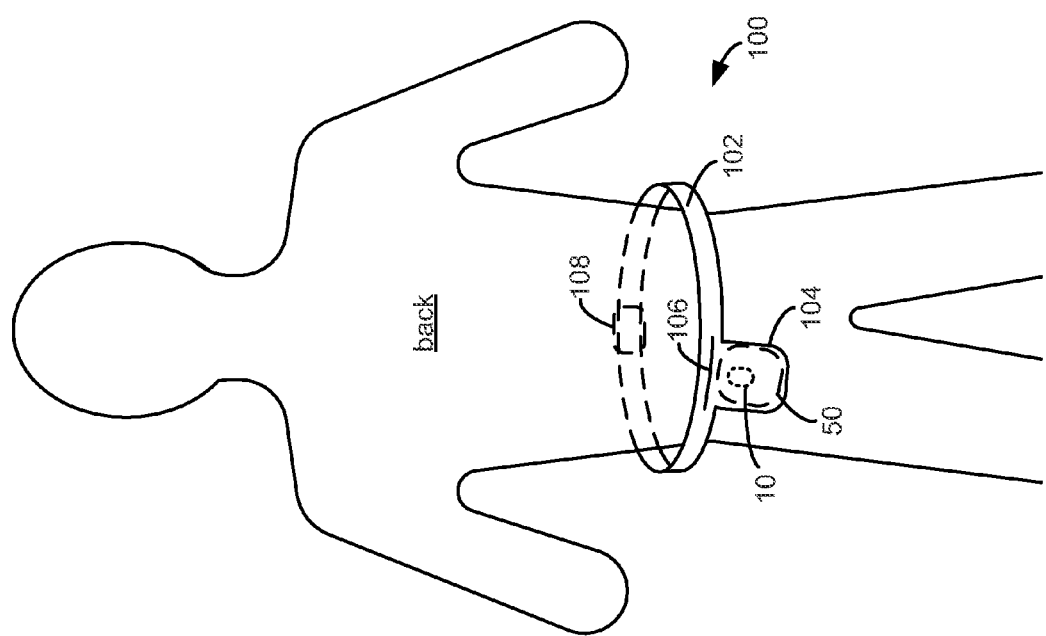
FIG. 3 shows a holding device used to affix the external charger to a patient in accordance with the prior art.

Thus, charging system 200 is self-affixing to the patient to allow for charging of the patient's IPG 10 unassisted by an additional holding device, such as a belt. The charging system can be put on and removed easily by bending, and does not use fastening means (compare 108; FIG. 3), which can be difficult for patients with limited dexterity or mobility to use, and which can break or wear out.

Additionally, separating the charging coil 250 from the electronics module 210 reduces heating concerns. With the conductive structures in the electronics module 210 positioned remotely from the charging coil 250 and hence the magnetic charging field, Eddy currents are less likely to form in such structures. As such, heating is mitigated, and power is thus more efficiently transferred to the IPG 10. Reduced heat also allows for the use of larger diameter charging coils 250, which eases alignment between the coil 250 and the IPG 10. An example diameter for the charging coil 250 may comprise approximately 4.5 inches.

The shape and flexibility of charging system 200 readily allows for the powering of implants implanted in other locations of a patient 350. For example, FIG. 9 shows an IPG 10 implanted under the collar bone on the front side of a patient 350's body, as is typical in a Deep Brain Stimulation (DBS) application. Two different examples of how the charging system 200 can be affixed to the patient 350 are shown. To the left, the flexible member 220 has been bent and placed over the patient's shoulder, with the coil module 215 aligned with the IPG 10 on the front side, and with the electronics module 210 running down the patient's back. Because the weights of the two modules 210 and 215 are comparable (or can intentionally be made that way), the charging system 200 will naturally rest in this position, even while the patient 350 is walking. On the right side of FIG. 9, the flexible member 220 has been bent and placed around the patient's neck, with the coil module 215 aligned with the IPG 10 on the front side, and with the electronics module 210 placed on the other side of the patient's chest. If the flexible member 220 is longer, it may be bent to drape down the patient's back before turning around the neck and over the patient's other shoulder. The flexible member 220 can again be bent to slightly pinch the charging system 200 against the patient 350, and/or gravity can assist in affixing the system to the patient, either option providing the necessary affixing force.

The charging system 200 can also be used to charge implants implanted in other locations. If the flexible member 220 is made long enough to affix the charging system 200 to the largest portions of the patient's body, e.g., around the waist, then smaller body portions can be easily accommodated. For example, if a patient has an implant in his leg or arm, the flexible member 220 can be wound (e.g., spiraled) around the leg or arm to affix the system 200 to the patient. If a patient has an implant in his head, the flexible member 220 could be wrapped around the head or the neck, depending on which configuration would be most comfortable and best able to affix the system 200 to the patient. Especially if gooseneck tubing is used for the flexible member 220, the flexible member 220 can be bent in all directions, although other flexible members 220 may also be used that are only flexible in one dimension. Furthermore, gooseneck tubing will allow for some degree of rotation of the modules 210 and 215 with respect to each other. Optionally, the modules 210 and 215 can be affixed to the flexible member 220 to allow them to rotate with respect to the flexible member 220, therefore allowing the patient further flexibility in affixing the charging system 200 in comfortable positions while still maintaining good alignment to their IPG 10. If the modules are made to rotate in this fashion, care should be taken to provide slack in any wires that may run through or along the flexible member 220.

The flexible member 220 can also be made adjustable in length, and so can be sized appropriately for a particular charging application and patient. For example, although not shown, flexible member 220 could comprise two separate flexible members (e.g., goosenecks tubes) with different diameters to allow one to slide into the other to adjust the overall flexible member length. The two goosenecks could then hold this length either by friction (like in a telescoping antenna), or could be screwed together. Shortening of the length of the flexible member 220 may cause the fabric of the sleeve 220 to "bunch up," but this is not problematic.

Another advantage of charging system 220 is that it generally allows visual aspects of the user interface 237 to be seen by the patient 350, regardless of where an implanted has been implanted in a patient. Consider FIG. 8 again: the IPG 10 is implanted in the back of the patient, and therefore were the patient to use a traditional external charger 50 (FIG. 2), the patient would not be able to see the user interface 70 (e.g., switch 72 and LED 74). However, because the electronics module 210 containing the user interface 237 is now in front of the patient, it can be easily seen and manipulated by the patient. This means that visual user interfaces are rendered more useful in charging system 200, opening the possibility of expanding such interfaces. For example, the electronics module 210 could be provided with a graphical user interface 310 with a display (FIG. 7), similar to that used in the external controller 152 of FIG. 4, to improve the patient's experience.

Figure 10A:
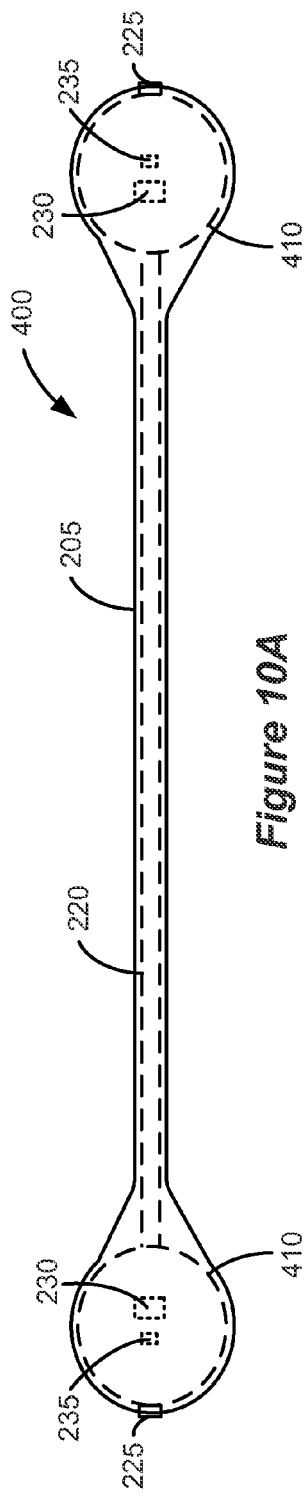
FIGS. 10A-10C show an alternative embodiment for the improved charging system having a flexible member adjoining two charging modules each independently capable of charging an IPG.
Figure 10B:
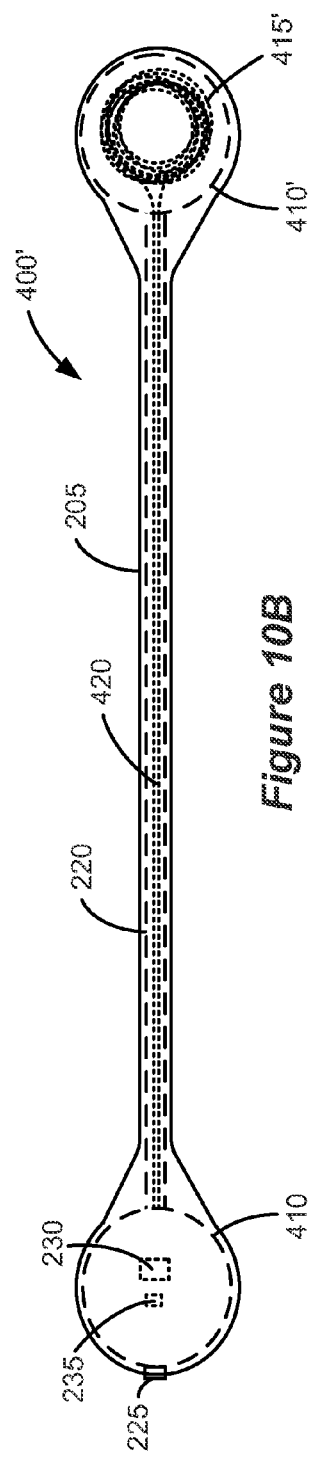
Figure 10C:
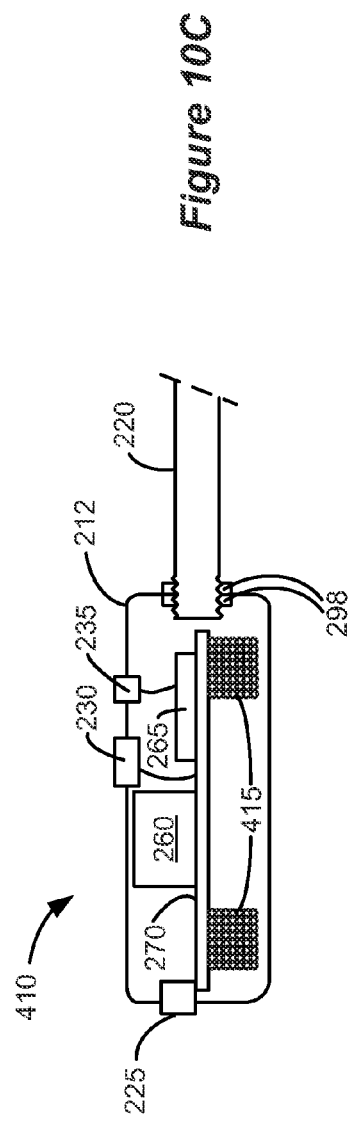

Modifications to the charging system 200 are possible. While it is preferred to separate the electronics and the charging coil 250 to reduce heating, this is not strictly necessary, and FIGS. 10A-10C illustrate an alternative charging system in which the electronics and charging coil 250 are incorporated together in a single module 410. In FIG. 10A, the charging system 400 comprises two charging modules 410, each of which is individually capable of charging an IPG 10 in its vicinity. The charging module 410, as shown in FIG. 10C, essentially comprises the same components of the electronics module 210 described earlier, but is modified to include a charging coil 415 on the underside of the PCB 270, similar to the external charger 50 of FIG. 2. In FIG. 10A, the charging module 410 is provided at both ends of the flexible member 220, with each module acting independently to charge two different IPGs. As FIG. 10C shows, each charging module 410 comprises its own battery 260, charging circuitry 265, on/off switch 230, LED 235, and port 225. The modules 410 are connected by flexible member 220, which allows for the system 400 to be bent and affixed to the patient to charge two IPGs 10, wherever they are implanted in a patient's body. Because the two charging modules 410 are independent in FIG. 10A, they need not communicate, and no wires are seen passing through or along flexible member 220. Charging module 410 may also contain one or more temperature sensors such as thermistors 295 (FIG. 7), but this is not shown for convenience.

Charging system 400' of FIG. 10B is also capable of charging two different IPGs. However, in this embodiment, the charging modules are different at each end of the flexible member 220. Charging module 410 is as discussed in FIG. 10C, and includes a battery 260, charging circuitry 265, on/off switch 230, and an LED 235, and a port 225. Charging module 410', by contrast, only contains a charging coil 415', and lacks a battery 260, charging circuitry 265, on/off switch 230, LED 235, and port 225. Charging module 410' acts as a slave to the master charging module 410, and is controlled and powered by the charging module 410. As such, wires 420 are passed from charging module 410 to charging module 410' to allow the former to controller charging of the latter. Wires 420 connect to the ends of charging coil 415', and additional wires could also be provided to carry other signals (such as wires carrying signals from thermistors 295; see FIG. 7).

FIG. 11 shows a DBS application in which charging systems 400 or 400' are useful. As is known, a DBS application can involve the implantation of two IPGs 10 and 10' under the patient 350's left and right collar bones, each servicing left and right sides of the patient's brain. As both IPGs 10 and 10' will need to be powered or recharged, charging system 400 or 400' (400' is shown) can be used to this end.

Figure 12A:
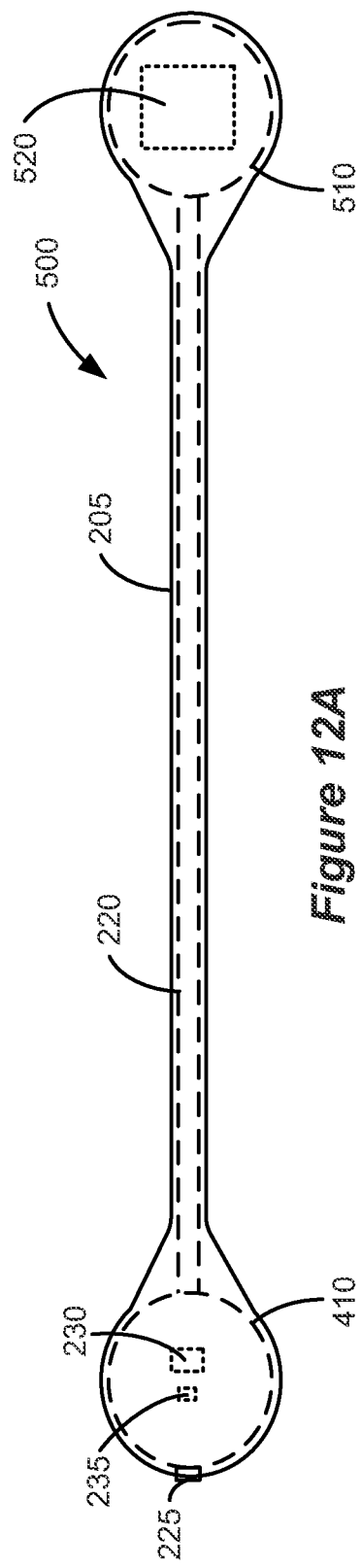
FIGS. 12A and 12B show an alternative embodiment for the improved charging system having single charging module adjoined to one end of a flexible member.
Figure 12B:
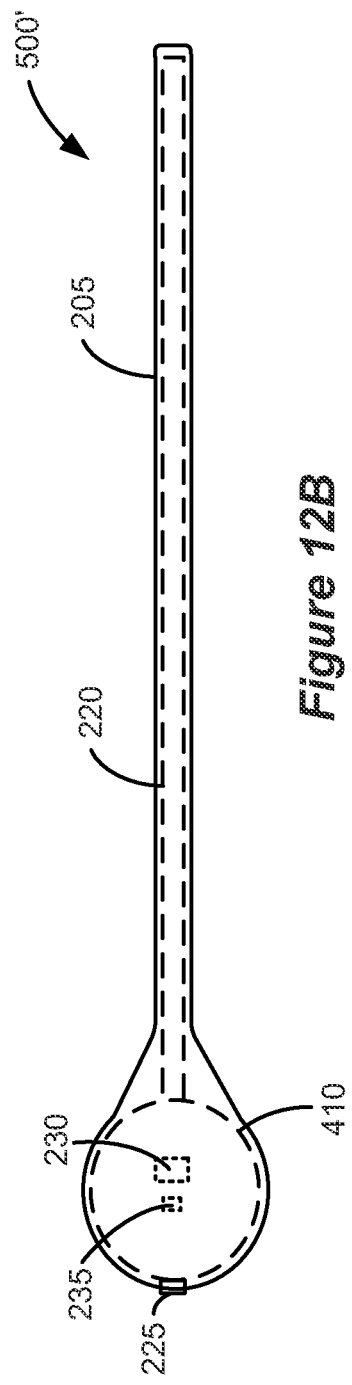

FIGS. 12A and 12B illustrate other modifications to the charging system, which incorporate a charging module 410 attached to only a single end of the flexible member 220. As such, the charging systems of FIGS. 12A and 12B would typically be used to charge a single implant in a patient. (This is not strictly true, as a single charging system can be used to charge multiple implants implanted in the same general vicinity in a patient. See, e.g., U.S. Patent Application Publication 2001/0121777). In FIG. 12A, charging system 500 comprises a weight module 510 opposite charging module 410, which includes a weight 520. The additional weight 520 in weight module 510 can be helpful to affix charging system 500 to a patient 350. For example, in the SCS application of FIG. 8, weight 520 helps add to the force F between the modules at the ends of the charging system, which helps to affix the charging system to the patient. In the DBS application of FIG. 9, weight 520 can counter the weight of module 410, which, as well as stabilizing the charging system on the patient's shoulder or neck, will also add to the gravitational force that assists in affixing the charging system to the patient.

In the charging system 500' of FIG. 12B, a charging module 410 is used at one end of the flexible member 220, but the other end does not contain a module. Still, charging system 500' is still self-affixing to the patient to allow for charging a patient's IPG 10 without the use of other holding devices. As mentioned earlier, the flexible member 220 can be bent or wrapped around a patient's waist, arm, leg, head, etc., to affix the charging system 500' to a patient. In essence, charging system 500' is similar to the prior art external charger 50 of FIG. 2, but attached to a flexible member 220, which obviates the need for a holding device.

Although particular embodiments of the present invention have been shown and described, it should be understood that the above discussion is not intended to limit the present invention to these embodiments. It should be clear to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A charging system for implantable medical devices, comprising:
   a flexible support;
   a coil positioned within a housing, wherein the housing is coupled to a first end of the flexible support; and
   an electronics module comprising circuitry configured to activate the coil to produce a charging field to charge or power an implantable medical device,
   wherein the flexible support comprises a structural support configured to hold a position when bent to affix the charging system to a patient.

2. The system of claim 1, wherein the structural support is a metal tube.

3. The system of claim 2, wherein the metal tube comprises a gooseneck tube.

4. The system of claim 1, wherein the flexible support is non-conductive.

5. The system of claim 1, further comprising wires to couple the coil to the circuitry.

6. The system of claim 5, wherein the wires pass through the flexible support.

7. The system of claim 5, wherein the wires pass alongside the flexible support.

8. The system of claim 1, further comprising a sleeve for enclosing the flexible support, the housing, and the electronics module.

9. The system of claim 1, wherein the electronics module comprises an on/off switch.

10. The system of claim 1, wherein the electronics module comprises a battery.

11. The system of claim 10, wherein the electronics module comprises a port configured at least to allow the battery to be recharged.

12. The system of claim 10, wherein the battery powers the circuitry.

13. The system of claim 1, wherein the flexible support is configured to affix the charging system to the patient by applying a force against the patient.

14. The system of claim 1, wherein the electronics module comprises a user interface.

15. The system of claim 1, wherein the housing further comprises a temperature sensor for communicating temperature information to the electronics module.

16. The system of claim 1, further comprising a weight at a second end of the flexible support.

17. The system of claim 1, further comprising:
   a second housing coupled to a second end of the flexible support, wherein the second housing comprises a second coil configured to produce a second charging field to charge or power an implantable medical device.

18. The system of claim 17, wherein the circuitry is coupled to the second coil, wherein the circuitry is configured to activate the second coil to produce the second charging field.

19. The system of claim 17, wherein the first and second coils operate independently.

20. The system of claim 1, wherein the electronics module is attached to the flexible support.

* * * * *